(12) United States Patent
Richter et al.

(10) Patent No.: US 6,426,439 B1
(45) Date of Patent: Jul. 30, 2002

(54) CONTINUOUS PROCESS FOR THE PREPARATION OF PENTAFLUOROETHYL IODIDE

(75) Inventors: Hans-Bodo Richter; Norbert Paul; Rudolf Huber, all of Burgkirchen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/462,115

(22) PCT Filed: Jun. 26, 1998

(86) PCT No.: PCT/EP98/03909

§ 371 (c)(1),
(2), (4) Date: Dec. 30, 1999

(87) PCT Pub. No.: WO99/01412

PCT Pub. Date: Jan. 14, 1999

(30) Foreign Application Priority Data

Jul. 4, 1997 (DE) .......................................... 197 28 560

(51) Int. Cl.$^7$ .............................................. C07C 19/08
(52) U.S. Cl. ...................................................... 570/161
(58) Field of Search .......................................... 570/161

(56) References Cited

U.S. PATENT DOCUMENTS

| 3,006,973 A | 10/1961 | Hauptschein et al. |
| 3,406,214 A | 10/1968 | Blochl |
| 3,821,321 A | 6/1974 | Hellberg et al. |

FOREIGN PATENT DOCUMENTS

| JP | 60/023333 | 5/1985 |

*Primary Examiner*—Alan Siegel
(74) *Attorney, Agent, or Firm*—Scott E. Hanf

(57) ABSTRACT

Continuous process for the preparation of pentafluoroethyl iodide from iodine, iodine pentafluoride and tetrafluoroethylene, which comprises dissolving the iodine in iodine pentafluoride and continuously feeding the resulting solution to a vertical bubble column (1), which is filled with iodine pentafluoride and at its lower end has a feed line for tetrafluoroethylene, where the reaction zone is maintained at from 85 to 95° C., preferably 90° C., and the pentafluoroethyl iodide formed escapes in gaseous form at the top of the reactor (1), is liquefied in a downstream cooled condenser and is drawn off into storage vessels.

5 Claims, 1 Drawing Sheet

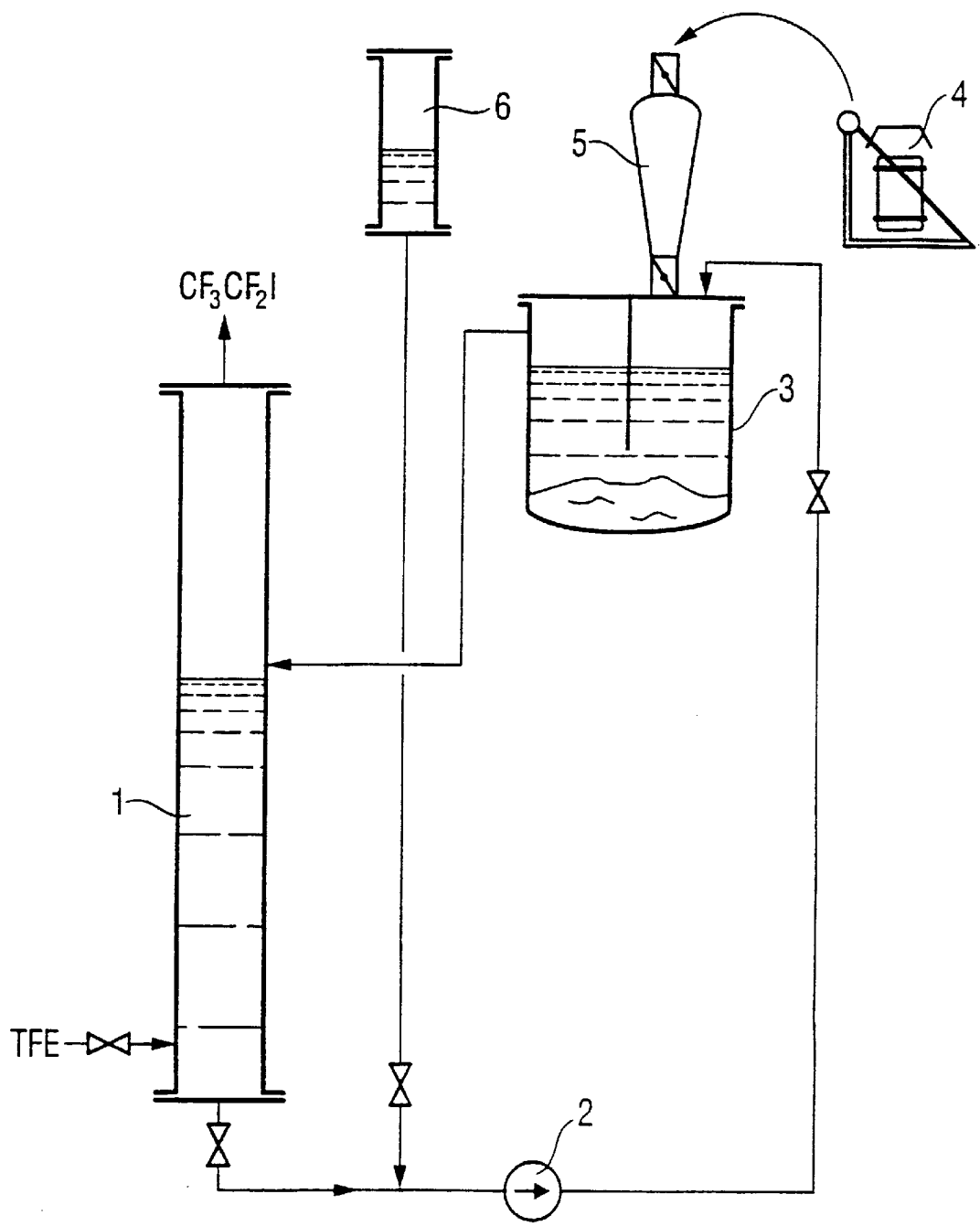

CONTINUOUS PROCESS FOR THE PREPARATION OF PENTAFLUOROETHYL IODIDE

This application is a 371 of PCT/EP/98/03909 filed Jun. 26, 1998.

DESCRIPTION

Pentafluoroethyl iodide is a valuable synthon for introducing the pentafluoroethyl group into organic compounds which, for example, have herbicidal action. However, pentafluoroethyl iodide has achieved greatest significance as a telogen in socalled telomerization with tetrafluoroethylene and/or hexafluoropropene. The perfluoroalkyl iodides which form in the process are important starting materials for numerous syntheses, which give active ingredients having strongly marked hydrophobic and oleophobic properties.

Pentafluoroethyl iodide is prepared predominantly in accordance with equation (I) below from tetrafluoroethylene, iodine pentafluoride and iodine:

$$5CF_2=CF_2 + IF_5 + 2I_2 \rightarrow 5CF_3CF_2I \tag{I}$$

A corresponding process is described, for example, in U.S. Pat. No. 3,406,214. It involved reacting a mixture of iodine pentafluoride and 10% by weight of iodine with gaseous tetrafluoroethylene at from 60 to 80° C. A conversion of 40% by weight and a yield of 90% by weight of pentafluoroethyl iodide were achieved.

There has been no lack of attempts to accelerate the preparation process according to the above equation (I) using catalysts, in particular using catalysts from the group of Lewis acid metal compounds, for example $TiCl_4$, $ZrCl_4$ or $VF_5$ (see DE-C-20 33 755). However, a disadvantage of this and similar processes is the increased rate of corrosion on the stainless steel apparatuses which are normally used.

In view of the potential hazard which originates in particular from the extremely reactive and toxic iodine pentafluoride, a preparation plant for pentafluoroethyl iodide by the process according to the equation (I) must satisfy particular requirements with regard to freedom from leaks and must have as few moving parts as possible. The addition of the iodine in liquefied form (by melting under pressure) has proven not to be recommended because of the corrosivity toward metallic materials; even nickel-based alloys are not completely durable during the storage of liquid iodine. Moreover, the exact metered addition of the pressurized, liquid, about 125° C.-hot iodine to the iodine pentafluoride, which is present in the reactor and has a temperature of about 90° C., has proven to be problematical.

There was therefore a great need for a safe and simple process for the preparation of pentafluoroethyl iodide according to equation (I). The object according to the invention is achieved. essentially by continuous dissolution of solid iodine in iodine pentafluoride. The flow diagram of the process is shown in the Figure. In detail, the process consists of the following steps: A vertical bubble column 1, which is equipped with a level regulator, is filled with $IF_5$ and heated to from 85 to 95° C., preferably 90° C. A defined amount of crystalline iodine is transferred from an iodine transportation container using a lifting and tilting device 4 into the charge transfer tube 5 and from there is passed batchwise to the iodine dissolution vessel 3 filled with $IF_5$. "Weakened" $IF_5$ is continuously passed into the iodine dissolution vessel 3 from the bubble column 1 using the circulation pump 2. The iodine dissolution vessel 3 is designed such that the filling with solid iodine and the introduction of the "weakened" $IF_5$ is separated from the overflow of the $IF_5$ concentrated with iodine by a calming zone. The $IF_5$ concentrated with iodine to the solution equilibrium is allowed to flow continuously via an overflow into the reactor 1, while tetrafluoroethylene is simultaneously introduced at the foot of the reactor 1 at the rate at which it is consumed by the reaction. Pure pentafluoroethyl iodide escapes at the top of the reactor 1, is liquefied in a cooled condenser and collected in a storage tank. The $IF_5$ consumed in the reaction is replenished, by means of a level regulator in the bubble column 1, from the storage container 6 via the pump 2 into the $IF_5$ cycle. The amount of solid iodine in the dissolution vessel 3 is determined by means of a radioactive level measurement. The solubility of iodine in iodine pentafluoride is 5.2% by weight at 20° C. and from 9 to 10% by weight at from 85 to 95° C.

The process according to the invention has the following advantages:

a) liquid iodine is not used. This avoids the serious problems which result from working with liquid iodine both in terms of process technology and with regard to industrial safety.

b) Apparatus, pipelines and fixtures can be made of customary chromium-nickel steels, for example steel 1.4571. This means significantly lower capital costs compared to liquid iodine processes.

c) The yield of pentafluoroethyl iodide is, in continuous operation, from 97 to 98% of the theoretical yield, based on $IF_5$. This corresponds to the best yield which has been achieved using Lewis acids such as $SbF_3$ or $PCl_5$ as catalysts (see JP-A-60/023333) . It is self-evident that a great advantage of the process according to the invention is that it can be carried out without Lewis acids or other catalysts.

What is claimed is:

1. A continuous process for the preparation of pure pentafluoroethyl iodide from iodine, iodine pertafluoride and tetrafluoroethylene, which comprises dissolving the iodine in a mixture which is separated from the lower end of a vertical bubble column (1) and continuously feeding the resulting solution to said vertical bubble column (1), which is equipped with a level regulator, is filled with iodine pentafluoride and at its lower end has a controllable feed line for tetrafluoroethylene, where the reaction zone is maintained from 85 to 95° C., and the pentafluoroethyl iodide formed escapes in gaseous form at the top of the reactor (1), is liquefied in a downstream cooled condenser and is drawn off into storage vessels.

2. The process as claimed in claim 1, wherein crystalline iodine is fed from suitable storage containers by means of a lifting and tilting device (4) to a charge transfer tube (5), from which the batchwise addition of the iodine into a dissolution vessel (3) takes place, where the iodine is dissolved in iodine pentafluoride.

3. The process as claimed in claim 1 wherein iodine pentafluoride is fed continuously at the rate at which it is consumed from a storage container (6) using a pump (2) to the circuit which leads via the iodine dissolution vessel (3) to the reactor (1).

4. The process as claimed in claim 2, wherein iodine pentafluoride is fed continuously at the rate at which it is consumed from a storage container (6) using a pump (2) to the circuit, which leads via the iodine dissolution vessel (3) to the reactor (1).

5. The process as claimed in claim 1 wherein the reaction zone is maintained at 90° C.

* * * * *